US00PP26609P3

(12) United States Plant Patent
Miller

(10) Patent No.: US PP26,609 P3
(45) Date of Patent: Apr. 12, 2016

(54) ***SALVIA* PLANT NAMED 'KILLER CRANBERRY'**

(50) Latin Name: *Salvia microphylla*
Varietal Denomination: KILLER CRANBERRY

(71) Applicant: Luen Miller, Santa Cruz, CA (US)

(72) Inventor: Luen Miller, Santa Cruz, CA (US)

( * ) Notice: Subject to any disclaimer, the term of this patent is extended or adjusted under 35 U.S.C. 154(b) by 116 days.

(21) Appl. No.: 14/120,302

(22) Filed: May 13, 2014

(65) Prior Publication Data

US 2015/0334908 P1 Nov. 19, 2015

(51) Int. Cl.
*A01H 5/00* (2006.01)

(52) U.S. Cl.
USPC ..... Plt./475

(58) Field of Classification Search
USPC ..... Plt./475
See application file for complete search history.

*Primary Examiner* — Annette Para
(74) *Attorney, Agent, or Firm* — Cassandra Bright

(57) ABSTRACT

A new and distinct *Salvia* cultivar named 'KILLER CRANBERRY' is disclosed, characterized by glossy foliage, dark peduncles and pedicels, and strong magenta flower color, which resists fading. Plants form an attractive "V" shape, and respond well to pruning for cutting back. The new variety is a *Salvia*, normally produced as an outdoor garden or container plant.

2 Drawing Sheets

Figure 1:
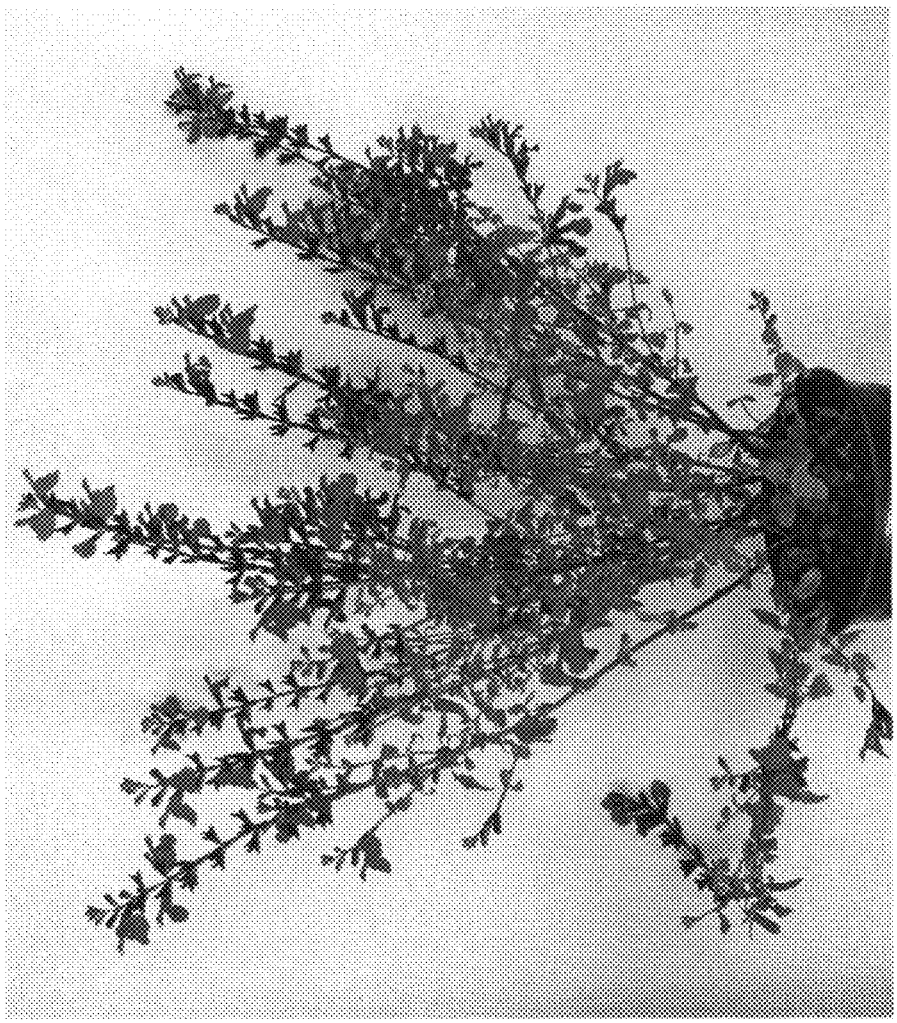

Latin name of the genus and species: *Salvia microphylla*.
Variety denomination: 'KILLER CRANBERRY'.

BACKGROUND OF THE INVENTION

The new *Salvia* cultivar is a product of chance discovery. The new variety was discovered as a chance seedling among a commercial planting of *Salvia microphylla* plants. The seed parent is believed to be *Salvia microphylla*, 'Hot Lips'. The pollen parent is unknown, but likely another *Salvia microphylla* variety. The new variety was discovered at a commercial nursery in Royal Oaks, Calif. during the Spring of 2010.

Asexual reproduction of the new cultivar 'KILLER CRANBERRY' by vegetative cuttings was first performed Apr. 4, 2012, at a at a commercial nursery in Royal Oaks, Calif. Subsequent propagation has shown that the unique features of this cultivar are stable and reproduced true to type on successive generations.

SUMMARY OF THE INVENTION

The cultivar 'KILLER CRANBERRY' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'KILLER CRANBERRY' These characteristics in combination distinguish 'KILLER CRANBERRY' as a new and distinct *Salvia* cultivar:

1. Glossy foliage
2. Dark, vibrant magenta flowers
3. Excellent plant response to cut back.
4. Strong flower color, resistant to fading.
5. Overall very attractive, inverted "V" shaped plant form 6. Distinctive dark peduncles and pedicels.

PARENT COMPARISON

Inventor is unable to verify the parent varieties.

COMMERCIAL COMPARISON

Plants of the new cultivar can be compared to the commercial variety *Salvia microphylla* 'RFD-S018', U.S. Plant Pat. No. 14,699. The two *Salvia* varieties are very similar in most horticultural characteristics, however, the new variety produces a more vibrant, deep magenta flower and a stronger and longer peduncle. Plants of the new variety respond better to cutting back, than the comparator, producing an attractive well branched plant. Foliage differs as well; the new variety has foliage with glossier appearance.

Plants of the new cultivar can be compared to the commercial variety *Salvia microphylla* 'Hot Lips', unpatented. The two *Salvia* varieties are very similar in most horticultural characteristics, however, the new variety produces an inflorescence with solid, magenta colored flowers, compared to the red and white flowers of 'Hot Lips'. Foliage differs as well; the new variety has glossier foliage.

Plants of the new cultivar can be compared to the commercial variety *Salvia microphylla* 'EGGEN005', U.S. Plant Pat. No. 24,151. The two *Salvia* varieties are very similar in most horticultural characteristics, however, the new variety differs in the following:

1. Inflorescence of the new variety is an average of 15 cm long, this comparator produces an average inflorescence of 8 cm.
2. The variety produces glossier foliage.
3. The new variety

BRIEF DESCRIPTION OF THE PHOTOGRAPHS

The accompanying photograph in FIG. 1 illustrates in full color a typical plant of 'KILLER CRANBERRY'.

Figure 2:
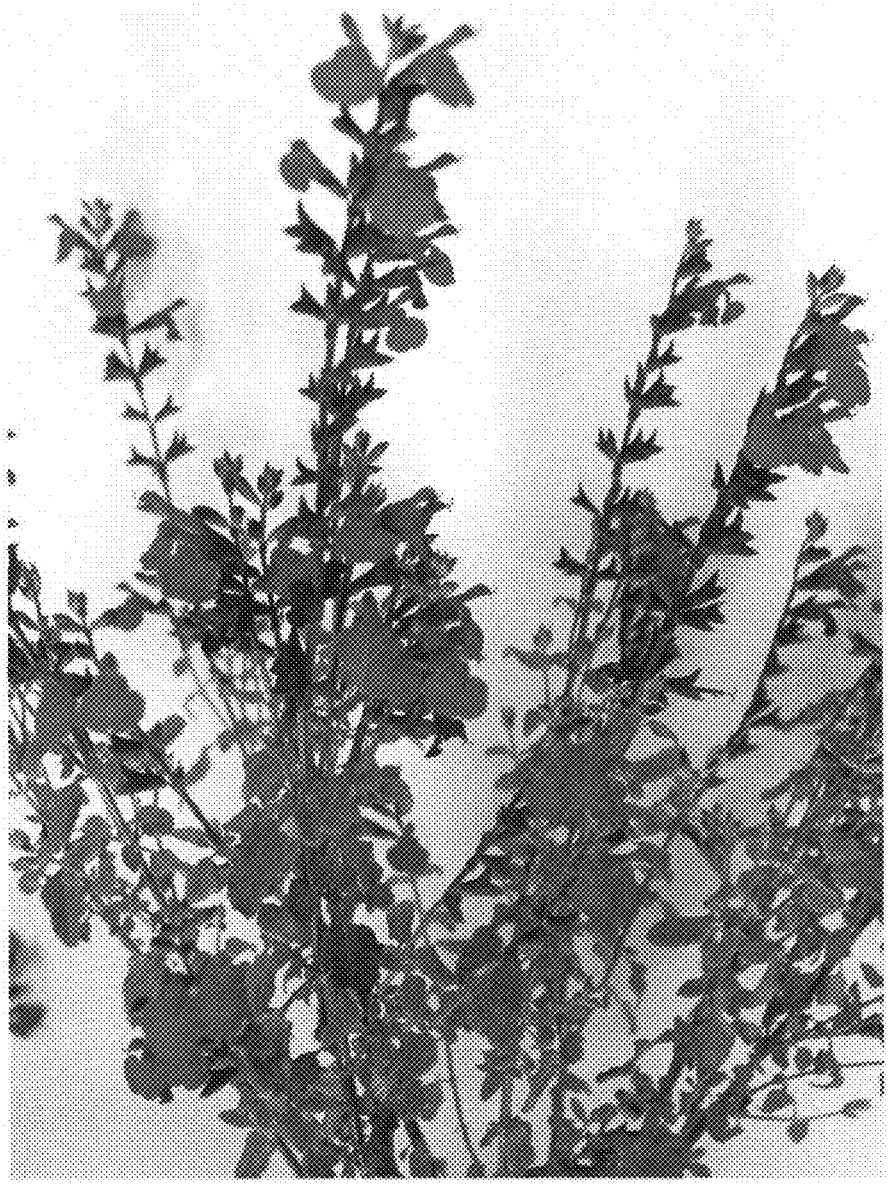

FIG. 2 illustrates in full color typical flowers of 'KILLER CRANBERRY'.

The plant was grown outdoors, in Royal Oaks, Calif. Age of the plant photographed is approximately 50 weeks from an unrooted cutting. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'KILLER CRANBERRY' plants grown outdoors in Royal Oaks, Calif. The growing temperature ranged from approximately 2° C. to 35° C. Measurements and numerical values represent averages of typical plant types.

Botanical classification: *Salvia microphylla* 'KILLER CRANBERRY'.

PROPAGATION

Time to initiate roots: About 5-8 days at approximately 25° C.

Root description: Fine, densely fibrous.

Time to produce a rooted cutting: About 21 days at 25° C.

PLANT

Growth habit: Upright, bushy annual.

Height: Approximately 30 cm to top of foliage. Approximately 50 cm to top of flowering plane. Measured from soil level of pot.

Plant spread: Approximately 45 cm.

Growth rate: Rapid.

Branching characteristics: Free-branching. Approximately 8 to 10 primary branches.

Length of primary lateral branches: Approximately 20 cm.

Diameter of lateral branches: Approximately 0.4 cm.

Quantity of lateral branches: About 12 to 18 main branches, each with an average of 10 additional sub-lateral branches.

Stem:

*Color.*—Closest to a color between Greyed-Purple N187A and 187A.

*Pubescence.*—Minute pubescence.

Internode length: Approximately 1.8 to 2.8 cm.

Age of plant described: Approximately 50 weeks from an unrooted cutting.

FOLIAGE

Leaf:

*Arrangement.*—Opposite.

*Quantity.*—Average 10 fully expanded per main branch.

*Average length.*—Approximately 3.5 cm., including petiole.

*Average width.*—Approximately 1.5 cm.

*Shape of blade.*—Obovate.

*Apex.*—Obtuse.

*Base.*—Obtuse to nearly truncate.

*Attachment.*—Stalked.

*Margin.*—Crenate.

*Texture of top surface.*—Faintly hirsute to the touch, hairs not visible.

*Texture of bottom surface.*—Smooth, faintly hirsute to the touch along mid vein.

*Color.*—Young, foliage upper side: Near RHS Green 138A. Young foliage under side: Near RHS Green 138B. Mature foliage upper side: Near RHS Green 137A. Mature foliage under side: Near RHS Green 138A.

*Venation.*—Type: Pinnate. Venation color upper side: Near RHS Yellow-Green 144A. Venation color under side: Near RHS Yellow-Green 145A.

*Petiole.*—Average Length: Approximately 0.6 cm. Diameter: Approximately 0.1 cm. Color: Near Yellow-Green 144A.

FLOWER

Natural flowering season: Flowering from early Spring through late Summer.

Inflorescence type and habit: Flowers arranged in verticillasters on spikes.

Flower longevity on plant: Individual flowers last approximately 10 days on the plant. Each spike lasts approximately 8 to 12 weeks with flowers.

Quantity of flowers: About 8 to 16 buds and 8 to 16 fully opened flowers per spike, at one time. A 1 year old plant has approximately 35 spikes per plant in full blooms.

Spike size:

*Diameter.*—Average 15 cm.

*Height.*—Approximately 4.8 cm.

Individual flowers:

*Size.*—Diameter: Approximately 1.7 cm. Length: Approximately 2.7 cm.

*Persistence.*—Non-persistent.

*Fragrance.*—Faint, typical *Salvia* scent.

*Corolla.*—Petal arrangement: The corolla is sympetalous and typically bilabiate with 2 small, highly fused lobes forming an upper lip and 3 larger highly fused lobes forming a lower lip. Margin: Entire. Tip shape: Upper lip tip retuse, lower lip tip rounded. Length: Upper lip Approximately 1.0 cm, lower lip Approximately 1.2 cm. Tube length Approximately 1.3 cm. Width: Upper lip Approximately 0.4 cm, lower lip Approximately 1.5 cm. Tube width Approximately 0.7 cm. Texture: Upper lip: Highly pubescent on exterior surface. Interior surface glabrous. Lower lip: Glabrous all surfaces.

*Color.*—Upper Lip: When opening: Inner surface: Near RHS Red-Purple N66D. Outer surface: Near RHS Red-Purple 61A. Fully opened: Inner surface: Near RHS Red-Purple N71A, deeper and brighter. Outer surface: Near RHS Red-Purple 72A, deeper and brighter. Fading: Inner surface: Near RHS Purple N78C. Outer surface: Near RHS Purple N77A.

*Color.*—Lower Lip: When opening: Inner surface: Near RHS Red-Purple N71A, deeper and brighter. Outer surface: Near RHS Red-Purple 72A, deeper and brighter. Fully opened: Inner surface: RHS Red-Purple 70B, center eye white N155B. Outer surface: RHS Red-Purple 70C, center eye white N155B. Fading: Inner surface: Near RHS Purple N78C. Outer surface: Near RHS Purple N77A.

*Color.*—Tube: When opening: Inner surface: Near RHS Red-Purple N66D. Outer surface: Near RHS Red-Purple 61A. Fully opened: Inner surface: Near RHS Red-Purple 72B. Outer surface: Near RHS Red- Purple 72B. Fading: Inner surface: Near RHS Purple 77A. Outer surface: Near RHS Purple 79C.

*Bud*.—Shape: Ovoid. Length: Approximately 1.5 cm. Diameter: Approximately 0.7 cm. Color: Near RHS Purple N79A.

*Calyx*.—Length: Approximately 1.4 cm. Diameter: Approximately 0.7 cm. Shape: Tubular.

*Sepals*.—Quantity per flower: 3, fused to form a tube. Unfused Apex: Length: Approximately 0.4 cm. Width: Approximately 0.3 cm. Margin: Entire. Apex: Acute. Texture: Pubescent. Color: Immature: Near RHS Green 137b, apex flushed Greyed-Purple N186A. Mature: Near RHS Greyed-Purple N186A.

*Peduncle*.—Length: Average range 3 cm to 8 cm. Diameter: 0.3 cm. Color: Near RHS Green 137b, apex flushed Greyed-Purple N186A. Orientation: Upright, straight. Strength: Strong. Texture: Pubescent, ridged.

*Pedicels*.—Length: Average 0.5 cm. Diameter: 0.1 cm. Color: Near RHS Greyed-Purple N186A. Orientation: Straight, approximately 35 degree angle from attachment. Strength: Flexible. Texture: Pubescent.

REPRODUCTIVE ORGANS

Stamens:

*Number*.—2.

*Filament length*.—Approximately 1.1, approximately 0.5 cm of length fused to petal.

*Filament color*.—Near RHS White N155B, flushed Purple 77A.

Anthers:

*Shape*.—Very narrowly elliptic.

*Length*.—Approximately 3 mm.

*Color*.—Near RHS Greyed-Purple N186A.

*Pollen*.—Scant colored near Yellow 13A.

Pistil:

*Number*.—1.

*Length*.—Approximately 2.1 cm.

*Color*.—Near RHS White N155A, upper Red-Purple 72B.

*Stigma*.—Shape: Linear, curled. Color: Near RHS Red-Purple N79A. Ovary color: Near RHS Yellow-Green 145C.

OTHER CHARACTERISTICS

Seeds and fruits: Not observed to date.

Disease/pest resistance: Neither resistance nor susceptibility to pathogens and pests common to *Salvia* have been observed.

Temperature tolerance: The new variety tolerates temperatures between 5° to 35° C.

What is claimed is:

1. A new and distinct cultivar of *Salvia* plant named 'KILLER CRANBERRY' as herein illustrated and described.

* * * * *